(12) United States Patent
Keely et al.

(10) Patent No.: US 6,703,831 B1
(45) Date of Patent: Mar. 9, 2004

(54) DUAL EDDY CURRENT PROBE FOR DETECTING GEOMETRICAL DIFFERENCES ESPECIALLY AS RELATED TO THREADED APERTURES AND STUDS

(75) Inventors: William A. Keely, Oxford, MI (US); Randall H. Field, Rochester Hills, MI (US)

(73) Assignee: Quantech, Inc., Pontiac, MI (US)

( * ) Notice: Subject to any disclaimer, the term of this patent is extended or adjusted under 35 U.S.C. 154(b) by 0 days.

(21) Appl. No.: 09/677,977

(22) Filed: Oct. 3, 2000

Related U.S. Application Data (60) Provisional application No. 60/164,994, filed on Nov. 12, 1999.

(51) Int. Cl.[7] .............................................. G01N 27/72
(52) U.S. Cl. ...................................... 324/232; 324/238
(58) Field of Search ................................ 324/232, 234, 324/238, 226, 227, 228, 241, 240, 243, 220, 237, 242

(56) References Cited

U.S. PATENT DOCUMENTS

| | | | |
|---|---|---|---|
| 2,353,211 A | * | 7/1944 | Zuschlag .................... 324/238 |
| 3,718,855 A | * | 2/1973 | Rogel et al. ................ 324/202 |
| 3,976,936 A | | 8/1976 | Nishino |
| 4,106,206 A | | 8/1978 | Piehl |
| 4,204,159 A | | 5/1980 | Sarian et al. |
| 4,413,231 A | | 11/1983 | Amedro et al. |
| 4,438,399 A | | 3/1984 | Schnabl et al. |
| 4,454,473 A | | 6/1984 | Rosauer |
| 4,629,984 A | | 12/1986 | Scalese |
| 4,788,499 A | | 11/1988 | Meier et al. |
| 4,855,677 A | | 8/1989 | Clark, Jr. et al. |
| 4,856,337 A | | 8/1989 | Metala et al. |
| 4,952,875 A | | 8/1990 | Adams et al. |
| 4,955,235 A | | 9/1990 | Metala et al. |
| 5,051,694 A | | 9/1991 | Dobler et al. |
| 5,056,016 A | | 10/1991 | Dobler et al. |
| 5,157,977 A | | 10/1992 | Grubbs |
| 5,859,370 A | | 1/1999 | Suh et al. |

* cited by examiner

Primary Examiner—Edward Lefkowitz
Assistant Examiner—Subhash A Zaveri (57) ABSTRACT

An apparatus and method for inspecting contours formed along a predetermined region of a surface on a workpiece formed of an electrically conductive material using eddy current. A probe includes a longitudinal axis and is moveable along a path of travel with respect to the predetermined region to be inspected on a workpiece. At least two coils are spaced longitudinally from one another and supported by the probe to be electrically excited with a predetermined frequency and amplitude during movement of the probe along the path. Sensors are provided for measuring the excitation voltage of each coil as eddy currents are induced in the electrically conductive material of the workpiece by the coils supported on the probe moving along the path of travel with respect to the workpiece. A comparison is performed between the measured eddy current signals from the at least two coils, where a non-zero difference after the coils have encountered the predetermined region to be tested represents an end position of the predetermined region formed on the workpiece being tested.

28 Claims, 3 Drawing Sheets

DUAL EDDY CURRENT PROBE FOR DETECTING GEOMETRICAL DIFFERENCES ESPECIALLY AS RELATED TO THREADED APERTURES AND STUDS

RELATED APPLICATIONS

This application is a continuation of U.S. Provisional Application Serial No. 60/164,994 filed Nov. 12, 1999.

FIELD OF THE INVENTION

The present invention relates to a dual coil eddy current probe for detecting geometrical differences especially as related to threaded apertures and fasteners or studs, and a method for detecting geometric differences using a dual coil eddy current probe.

BACKGROUND OF THE INVENTION

Several hundred apertures are drilled and tapped in a typical automobile engine and the various components associated with the engine. Additional apertures are required when other drive train components are included, such as suspension components, various brackets and levers, frame and sheet metal parts and the like. The process of drilling apertures and tapping or roll head formed threads in engine and drive train components does not result in perfect parts one hundred percent of the time. Quality control measures are required to test and verify the accuracy of the apertures and threads, either through a statistical sampling methodology, or through one hundred percent inspection of each drilled and tapped aperture or roll head formed thread. In many manufacturing environments, one hundred percent testing of all drilled and tapped apertures or roll-formed threads is impossible due to time constraints. In such instances, an aperture may be tapped with less than the minimum number of threads, or a damaged tap may create poorly formed threads, or worse yet, an aperture may not get tapped at all. In some instances, a tap can break off in the aperture. When such a component is transferred to the next operation or department, or worst of all, to the customer, substantial problems and costs inevitably result.

Relatively few machine builders have recognized the need for one hundred percent thread inspection following tapping operations, and most leave the inspection responsibility to the engine and drive train component manufacturers. Component manufacturers have dealt with the need to inspect threaded apertures in a variety of ways ranging from visual inspection by an operator to various forms of automated systems. Such automated systems are typically retrofitted as part of the tapping equipment, or immediately following the tapping operation as a separate step. If tapping equipment is originally equipped with thread detection, or if retrofitted, no loss in productivity occurs. If threads are detected off the production line, additional effort may be required.

With an increasingly quality driven environment at all levels of manufacturing in the world, the first efforts to inspect threaded apertures involve visual inspection by an operator of bolts or gauges actually threaded into the aperture as part of the inspection process. It quickly became evident that the human element could not be relied on or simply could not visually perform the necessary inspection due to lapse of attention, aperture depth, and so forth. Furthermore, threading a gauge into every aperture by hand was impractical at required production rates as well as relying on the human element to both read the difficult scales on such devices and to make consistent judgements as to acceptable threading torque thresholds. Enormous manpower was required to thread a bolt into every aperture by hand and this proved economically infeasible. It was recognized that a fast, consistently reliable approach was needed to inspect one hundred percent of the apertures for proper threads. Several contact and non-contact methods were developed involving quite different technologies ranging from mechanical feelers to reflective light to airflow/back pressure to electro-magnetic inspection.

Mechanical feelers are occasionally used to contact the inside edge of the aperture in order to sense movement when the feeler is moved actually within the aperture. This method determines that there are threads present on at least one side of the aperture, but does not determine much more than that. Therefore, this method has limited applications, and is not desirable for most inspection purposes.

Reflected light is another method used to detect threads. This is a non-contact, relatively quick inspection technique. It typically uses a sender/receiver probe that can be placed at an angle close to perpendicular to the face of the threads. As a light beam is directed toward the threads, the newly machined or formed surface reflects the light back to the receiver. If a sufficiently high reflectivity is present, a determination is assumed that a machined or formed surface representing threads is present in the aperture with the added assumption that the tap or roller former did the required work. With the ever present abundance of cutting fluids and coolants as well as washing fluids, both the sender and receiver units can degrade in performance. As both sending optics and receiving optics become obscured degrading optical transparency. Varying levels of reflectivity can affect detection capability when threads have fluids or oils deposited on the threads. Also, looking at only a small portion of the threaded aperture and assuming that properly formed threads are present in the rest of the aperture is not accurate in many cases, and does not form an adequate basis for accepting the aperture.

Another approach involves the use of an airflow/back pressure measurement. In this method, a probe is inserted into the aperture and injects air into the aperture. A sensor measures the back pressure of this flow as the air escapes. The turbulence created by the presence of threads causes an increase in back pressure over the back pressure present in the absence of threads, and thus the presence or absence of threads can be inferred. These systems are not adept at determining the actual number of threads to any degree of accuracy.

With the advent of smaller, better performing cameras and software, vision has been adapted for use in detecting the presence of threads in apertures. The environment of cutting fluids and oils on the cutting threads and within the aperture has a pronounced effect on the sensitive lighting requirements of the vision systems. In addition, not all threads are typically viewed with a vision system, and the assumption is made that the unseen threads are present and properly formed.

Another non-contact approach discloses the use of electromagnetic sensing using eddy currents. A probe having a single coil is excited at a specific frequency and is positioned in the aperture. The inductance of the coil plus the threaded aperture is sensed and compared to the inductance of the coil plus a known conforming threaded aperture. Since the inductance of the coil and aperture combination is affected by the combined geometry, among other things, similar geometries will exhibit similar inductance levels. By alternating current through a coil at a specific frequency and amplitude, and bringing the coil within close proximity of a part made of an electrically conductive material, the coil-part combination exhibits a combined inductance (measured in henries) as electrical currents known as eddy currents are induced in the surface of the part. The inductance of this part-coil combination is affected by primarily four characteristics of the material: microstructure/hardness; chemistry; temperature; and geometry. Since non-destructive testing using eddy currents is a comparative method, by placing the coil in the same position relative to another part, the inductance of this second combination is compared to the first one and differences can be detected. If the parts are of the same material at the same temperature, geometry differences can be very effectively detected. Thus, a tester using eddy current technology is calibrated using a known conforming part or master and then is used to detect differences in other materials relative to the geometry. Depending on the sophistication of the electronics sensing these inductance differences, more than just the presence or absence of threads can be detected. A simple, un-tuned type probe transducer circuit can, under ideal conditions, detect threaded conditions where as little as two or three threads are missing. Furthermore, the probes are unaffected by cutting fluids and coolants. The method is non-contact. The method detects 360° of geometry and is very quick to perform. Since this method involves inspecting the aperture at a discreet position within the aperture, the probe may inspect only those threads in the immediate vicinity of the coil on the probe, and ignores the other areas of the aperture that are supposed to be properly threaded.

Another use of eddy current technology involves the use of significantly different electronics and a tuned transducer probe. This approach was developed within the last few years and is purported to have between three to ten times the sensitivity compared to the untuned version. The probes are unaffected by cutting fluids. The method is non-contact, inspects in 360° of geometry, and is very quick to perform, approximately less than 0.1 second for the actual electronics and one to two seconds for a total cycling of the fixture actuator. The probe may not inspect threads in all parts of the aperture depending on the depth of the aperture. This method has the added advantage of being able to reliably detect one thread missing conditions in many applications due to the greater sensitivity. In most applications, the probe is advanced into the aperture while being held in a fixture with the part properly located. The fixture can use pneumatic actuators for the purpose of quickly moving the probe into and out of the aperture as controlled manually or via a programmable logic controller. The probe is positioned at the optimal depth within the aperture during each inspection in order to maximize the performance of the tuned transducer probe.

Another recent development in profiling the threaded aperture is an analog eddy current signal obtained as a function of depth into the aperture usually measured from the pierced surface. As the probe first enters the aperture, then passes through such features as counter-bores, then the threaded area itself, then into the unthreaded area of the pilot hole, the signal is continuously compared against an expected profile of a properly formed aperture. The probing coil can be concentric with the aperture centerline or it can be at 90° to the aperture centerline. In this second situation, the process gives up the ability to detect features in a full 360° of geometry, but can easily detect individual threads and provide the ability to count the threads. By alternating current (A.C.) coupling the probe, part to part variability challenges can be effectively negated. However, when threads need to be detected for a full 360° geometry, another technique must be relied on.

SUMMARY OF THE INVENTION

To further improve on the single coil probe approach, the present invention includes a dual coil element probe and support electronics. This provides enhanced electromagnetic thread detection. While the above-described, tuned probe, eddy current method has excellent performance for the vast majority of applications, in a few of these applications the conforming part population exhibits a greater spread of eddy current signatures. This is due to part-to-part variations in chemistry, microstructure/hardness, and possibly temperature and/or porosity. In these situations, while using a single coil, tuned probe, it can be more challenging to separate the non-conforming parts from the conforming part population, especially if relatively minor defects are to be found. By using a tuned, dual coil probe, differences in part-to-part chemistry and microstructure/hardness are very effectively eliminated, as are temperature variations. The present invention provides a greatly improved ability to ignore conforming part variations where function is not compromised, while at the same time, retaining an extremely effective ability at detecting thread depth, thread quality, and part porosity. The dual coil probe can be positioned at a specific depth where the probe will not only sense the presence of threads, but the thread quality and the thread depth to within one thread or less, or the probe can be combined with a linear variable differential transformer (LVDT) to sense the relative position of the dual coil probe with respect to the pierce surface of the part. This configuration provides full aperture profiling capability to the user. All features, such as counter bore presence, counter bore depth, and thread quality throughout the aperture including thread depth can be detected. The present invention allows detection of these characteristics while eliminating concern about occasional variations in materials and temperatures that can sometimes limit such detection capabilities. An advantage of the dual coil probe according to the present invention is in determining the depth of threads in a part population that can vary with respect to temperature, chemistry, and microstructure/hardness, or where frequent re-calibration of the tuned, single coil probe is not likely to be performed. The dual coil probe can accomplish inspection of the part population to within less than one thread, consistently and without frequent re-calibration.

Eddy current thread detection systems use both the phase shift and amplitude change of the electromagnetic signature that is induced in a sample by an inductor (transducer) to create a "transducer voltage." This transducer voltage relates basically to the electrical conductivity of a material and represents four material characteristics including: geometry; chemistry; case depth hardness/microstructure; and temperature. When the transducer is placed in an aperture which conforms to specifications, the transducer voltage is "learned" by the thread detection system electronics so that the "learned" transducer voltage can be used to compare it with other transducer voltages associated with apertures to be tested. While the transducer is properly positioned in an aperture, the detection system electronics creates an internal compensating voltage causing the transducer voltage to approach zero volts. The magnitude of the compensating voltage is stored in digital memory. As the transducer is placed in subsequent apertures, the compensating voltage is recalled and combined with the new transducer voltage. Each new sample voltage is displayed on the channel volt meter and compared to a threshold around the zero volt reference created during the learning process. The "window" adjustment allows the user to establish two thresholds around the "zero volts" reading with one threshold being positive in voltage and the second equally negative in voltage. If the transducer voltage of each new aperture falls between these two threshold values, the channel indicates conformance with the learned sample. If the transducer voltage is outside the two thresholds, the channel indicates non-conformance with the learned sample.

The present invention relates to the inspection of threaded apertures and threaded studs and is primarily used for quality control to evaluate the integrity of threads in or on electrically conductive parts. According to the present invention, parts are located and positioned relative to a probe. The probe includes two or more separate coils wound around an axis of the probe tip. The coils preferably are separated by a distance less than the depth or length of a threaded region to be inspected. The probe is moved into the aperture or onto the stud approximately along a centerline of the stud, so that the probe passes into the threaded region. The coils have a known electrical inductance and are electrically excited at a known frequency and amplitude. As the probe moves into and through the aperture or onto the stud, the amplitude and phase of the excitation voltage is extracted and measured for each coil as eddy currents are induced in the surrounding, electrically conductive material. These voltage amplitude and phase measurements can then be collectively or individually compared to analogous measurements taken while inspecting another part. The voltage amplitude and phase measurements can be subtracted and analyzed. The individual, collective, and /or subtracted measurements can be analyzed at a discreet point along the path of the probe during the inspection process, or the measurements can be analyzed on a continuous and/or segmented basis. The inspection process, according to the present invention, can include a linear variable differential transformer (LVDT) or linear potentiometer to measure the position of the probe along the axis, depth, or length of the aperture or stud. The apertures and studs can include tapped or machined threads, roll-formed threads, or blind apertures, through apertures, counter bores, and any combinations thereof. The present invention includes a probe with two or more separate coils and electronics sufficient to analyze the various amplitude and phase measurements. The present invention can include a linear variable differential transformer or linear potentiometer to measure depth or distance of probe travel and can also include a device to analyze the various amplitude and phase measurements on a continuous and/or segmented basis.

It is desirable in the present invention to provide a substantial improvement in the ability to distinguish between parts that are threaded to the fully desired depth or length and those that are threaded to a shorter or longer depth or length then possible using a probe with a single coil as previously known. It is desirable in the present invention to compare the various amplitude and phase measurements of one coil to the same measurements from one or more other coils in or on the same part. It is desirable in the present invention to provide more than one coil in the part region being inspected simultaneously in order to make a comparison between the coils. It is desirable in the present invention to be able to distinguish between conforming and non-conforming parts within a population of parts that are threaded to the fully desired depth or length while exhibiting variations in temperature, chemistry, and/or microstructure or hardness. The ability of a single coil probe and support electronics to compare a population of parts to a master part on the basis of those parts which are similarly threaded and those with less than the desired thread or depth of threads is limited because the various amplitude and phase measurements of the coil can be affected by the previously mentioned non-geometrical variations, such as temperature, chemistry, microstructure, and/or hardness. The dual coil probe, according to the present invention, effectively reduces or eliminates non-geometrical part-to-part variations and the comparison of measurements taken from one coil to those of the other coil or coils when both coils are used to inspect the same region of the same part.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
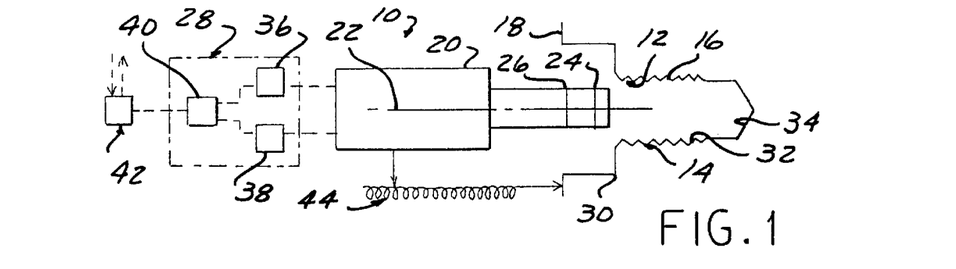
FIG. 1 is a simplified schematic view of an apparatus for inspecting contours formed along a predetermined region of a surface on a workpiece formed of an electrically conductive material using eddy current according to the present invention in a first position.
Figure 2:
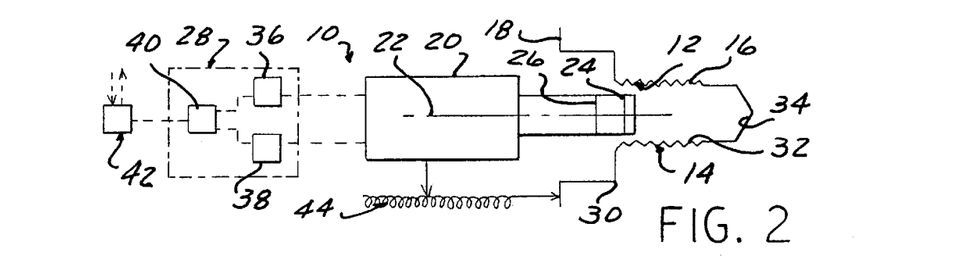
FIG. 2 is a simplified schematic view of a probe illustrated in FIG. 1 moved to a second position.
Figure 3:
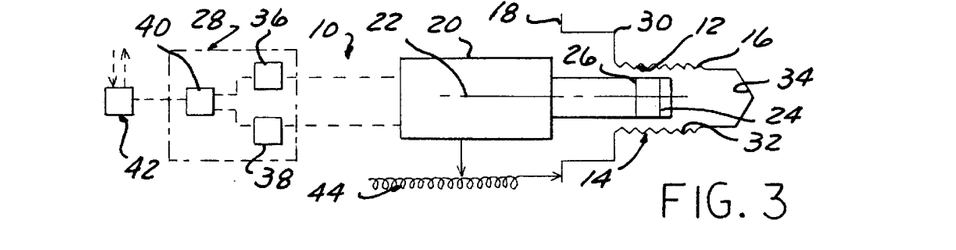
FIG. 3 is a simplified schematic view of the probe illustrated in FIGS. 1 and 2 moved to a third position.
Figure 4:
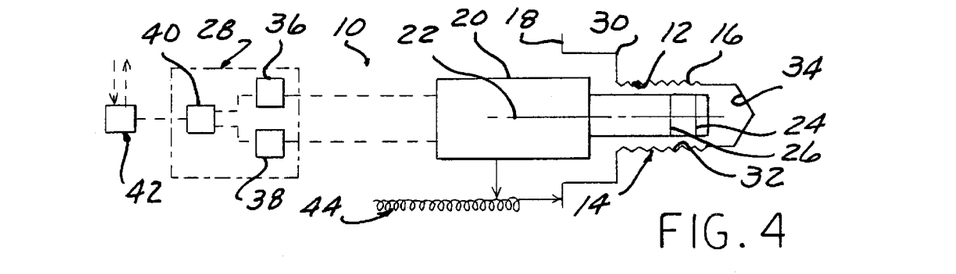
FIG. 4 is a simplified schematic view of the probe illustrated in FIGS. 1 through 3 moved to a fourth position.
Figure 5:
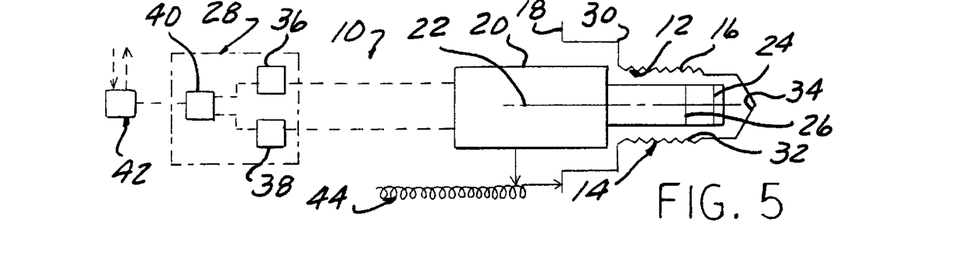
FIG. 5 is a simplified schematic view of the probe illustrated in FIGS. 1 through 4 moved to a fifth position.

Referring now to FIGS. 1 through 5, an apparatus 10 is illustrated for inspecting contours 12 formed along a predetermined region 14 of a surface 16 on a workpiece 18 formed of an electrically conductive material using eddy current. A probe 20 is illustrated in FIG. 1 in a first position and has a longitudinal axis 22. The probe 20 is moveable along a path of travel with respect to the predetermined region 14 to be inspected on the workpiece 18. Preferably, the path of travel extends along the longitudinal axis 22 of the probe 20. At least two coils 24, 26 are spaced longitudinally from one another and supported by the probe 20 to be electrically excited with a predetermined frequency and amplitude during movement of the probe 20 along the path of travel. Means 28 is provided for measuring the excitation voltage of each coil 24, 26 as eddy currents are induced in the electrically conductive material of the workpiece 18 by the coils 24, 26 supported on the probe 20 moving along the path of travel with respect to the workpiece 18. Preferably, the first and second coils 24, 26 are disposed coaxial with respect to one another along the longitudinal axis 22 of the probe 20. The contours 12 can include a counter-bore 30, and/or threads 32, and/or a pilot aperture 34.

The measuring means 28 can include a first voltage sensor 36 for measuring the excitation voltage of the first coil 24, a second voltage sensor 38 for measuring the excitation voltage of the second coil 26, and a comparator 40 for subtracting the excitation voltage sensed by the second voltage sensor 38 from the excitation voltage sensed by the first voltage sensor 36. A central control unit 42 can be provided for determining if the workpiece 18 being tested conforms to predetermined specifications in response to the measuring means 28. The central control unit 42 can include a central processing unit, microprocessor, or controller. The central control unit 42 provides means for comparing the measured eddy current signals from the at least two coils, 24, 26, where a non-zero difference after the coils have entered the predetermined region to be tested represents an end position of the contour, such as threads, formed on the workpiece being tested.

Figure 11:
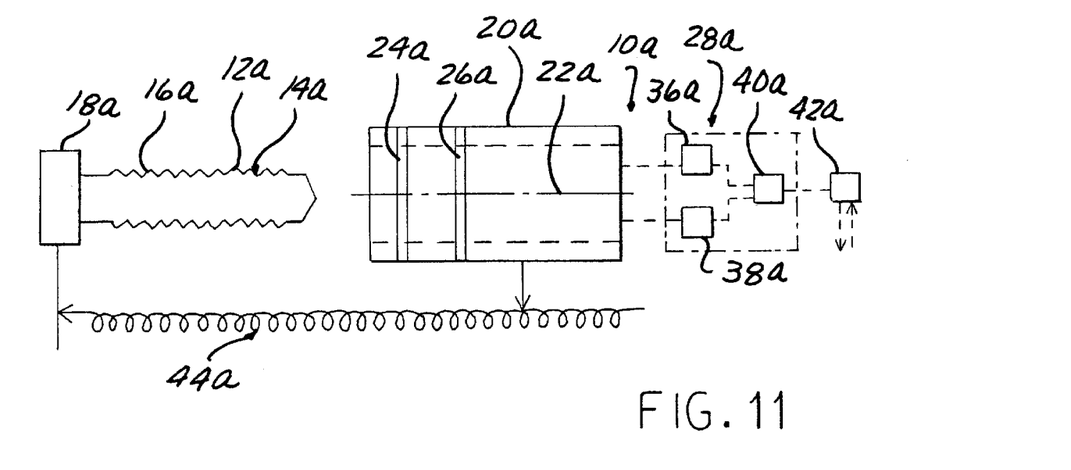
FIG. 11 is a simplified schematic view of an alternative embodiment of the apparatus for inspecting contours formed along a predetermined region of a surface on a workpiece formed of an electrically conductive material using eddy current according to the present invention.

A linear variable differential transformer or linear potentiometer 44 can be provided for measuring a position of the probe 20 as the probe 20 is being moved along the path of travel with respect to the workpiece 18. The probe 20 is illustrated in a first position in FIG. 1 with the longitudinal axis 22 of the probe 20 aligned with the longitudinal axis of the predetermined region 14, such as an aperture formed in the workpiece 18. The probe 20 is illustrated in a second position in FIG. 2 where the first coil 24 has moved into a predetermined region 14, such as the threaded region of the surface 16 on the workpiece 18. The probe 20 is illustrated in a third position in FIG. 3 where both coils 24, 26 have entered the predetermined region 14, such as the threaded region on the surface 16 of the workpiece 18. The probe 20 is illustrated in a fourth position in FIG. 4 where the first coil 24 has moved past an end position of the predetermined region 14, such as the threaded region on the surface 16 of workpiece 18, while the second coil 26 is still within the predetermined region 14. The probe 20 is illustrated in a fifth position in FIG. 5 where the first coil has moved beyond a predetermined region 14 and the second coil is on the verge of leaving the predetermined region 14, such as the threaded region on the surface 16 of workpiece 18. The embodiment illustrated in FIGS. 1 through 5 shows a probe 20 according to the present invention moveable within an aperture of the workpiece 18. It should be recognized that the present invention can be adapted to provide a probe 20a for movement to sheath a predetermined region 14a, such as a threaded region on the surface 16a of a shaft of a workpiece 18a as illustrated in FIG. 11.

Figure 6:
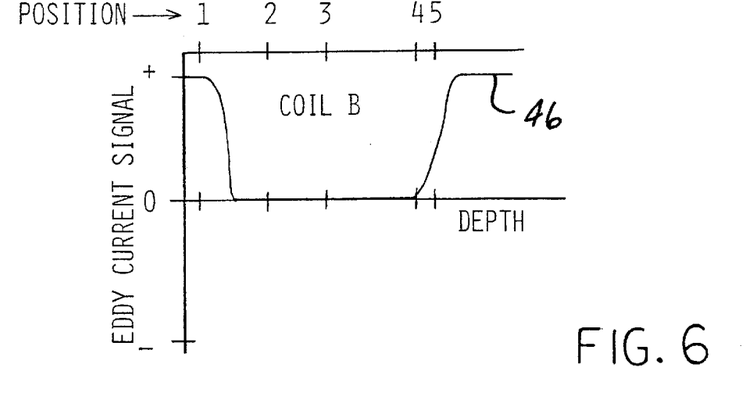
FIG. 6 is a graph illustrating an absolute value for an eddy current signal along a vertical axis versus probe depth or position along a horizontal axis with respect to positions 1 thorough 5 illustrated in FIGS. 1 through 5 for a first coil.
Figure 7:
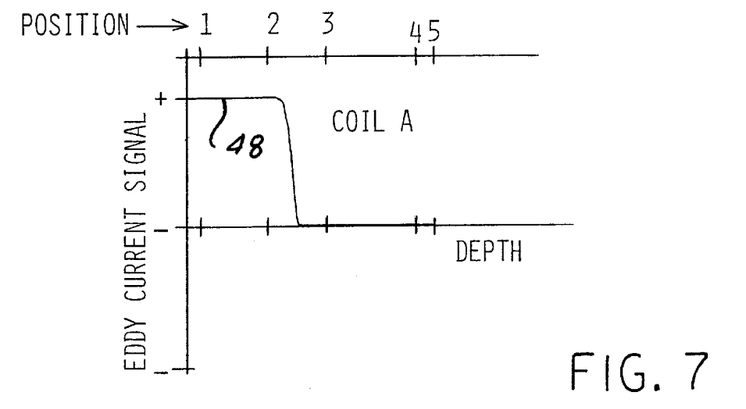
FIG. 7 is a graph illustrating an absolute value for an eddy current signal along a vertical axis versus probe depth or position along a horizontal axis with respect to positions 1 through 5 illustrated in FIGS. 1 through 5 for a second coil.
Figure 8:
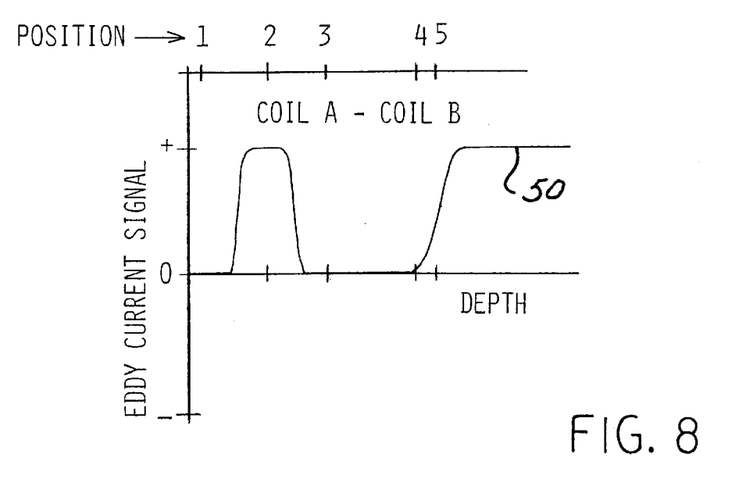
FIG. 8 is a graph illustrating an absolute value for an eddy current signal along a vertical axis versus probe depth or position along the horizontal axis for the probe with respect to positions 1 through 5 illustrated in FIGS. 1 through 5 where the first eddy current signal is subtracted from the second eddy current signal for comparison.

Referring now to FIGS. 6 through 8, graphs illustrate an absolute value for an eddy current along a vertical axis versus position or depth of the probe 20 with respect to the surface 16 on the workpiece 18 to be tested. The eddy current can be a positive or negative value depending on how the electronics are configured, and therefore the signals according to the present invention can also be represented as going to negative values rather than to positive values as shown in FIGS. 6 through 8. The positions 1 through 5 illustrated in the FIGS. 1 through 5 respectively, are noted on an upper horizontal axis of each graph. FIG. 6 illustrates the eddy current signal from the first coil 24 supported on the probe 20. The eddy current signal 46 illustrated in FIG. 6 begins with an absolute value positive signal that drops to a zero signal as the probe moves from position 1 illustrated in FIG. 1 to position 2 illustrated in FIG. 2. The eddy current signal remains at or near zero for the first coil 24 as the probe moves from position 2 illustrated in FIG. 2 through position 3 illustrated in FIG. 3 to position 4 illustrated in FIG. 4. When the probe 20 reaches position 4 illustrated in FIG. 4, the eddy current signal has begun to rise from zero to a positive value, or fall to a negative value, and continues to rise or fall as the probe moves from position 4 illustrated in FIG. 4 to position 5 illustrated in FIG. 5.

The eddy current signal 48 of the second coil 26 is illustrated in FIG. 7. The eddy current signal of the second coil 26 remains at a positive value as the probe 20 moves from the first position illustrated in FIG. 1 through the second position illustrated in FIG. 2. As the probe 20 moves from the second position illustrated in FIG. 2 to the third position illustrated in FIG. 3, the eddy current signal drops from the positive value to zero. The eddy current signal of the second coil 26 remains at zero as the probe 20 passes through the third position illustrated in FIG. 3, the fourth position illustrated in FIG. 4, and the fifth position illustrated in FIG. 5.

The eddy current signal 50 generated by the comparator 40 is illustrated in FIG. 8. The comparator 40 subtracts the eddy current signal 46 of the first coil 24 from the eddy current signal 48 of the second coil 26 to produce the eddy current signal 50 illustrated in FIG. 8. The eddy current signal 50 begins at zero when the probe 20 is at the first position, and rises to a positive eddy current signal when the probe 20 reaches the second position illustrated in FIG. 2. The eddy current signal 50 falls back to zero as the probe 20 moves between the second position illustrated in FIG. 2 and the third position illustrated in FIG. 3. The signal remains at approximately zero as the probe 20 moves between the third position illustrated in FIG. 3 and the fourth position illustrated in FIG. 4. As the probe 20 moves between the fourth position illustrated in FIG. 4 and the fifth position illustrated in FIG. 5, the eddy current signal 50 of the comparator 40 begins to, or continues to, rise above the zero value to a positive value corresponding to an end position of the contour formed in the workpiece being tested. The eddy current signal 50 illustrated in FIG. 8 is an example of an acceptable or conforming contour for the workpiece 18.

Figure 9:
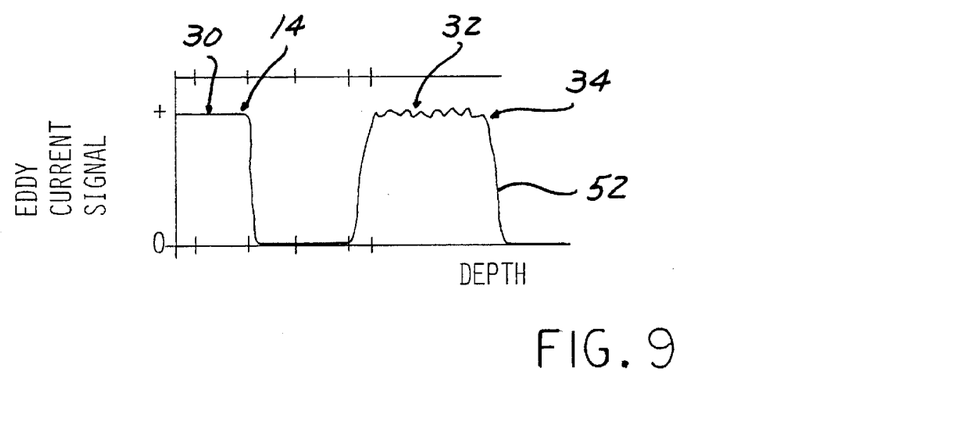
FIG. 9 is a graph illustrating an absolute value for an eddy current signal along a vertical axis versus probe depth or position along a horizontal axis for a dual coil probe according to the present invention showing a profile of an acceptable or conforming threaded aperture.

Referring now to FIG. 9, a graph illustrating an eddy current signal for a conforming contour 12 along a predetermined region 14 of a surface 16 formed on a workpiece 18 is illustrated. The graph illustrates an eddy current signal along the vertical axis and a position or depth of the probe 20 along the path of travel along the horizontal axis. The eddy current signal 52 begins with a positive signal portion corresponding to a counter-bore region. When the first coil 24 enters the predetermined region, the eddy current signal 52 drops from the positive value to a zero value. When the second coil 26 enters the predetermined region to be tested, the eddy current signal 52 rises from the zero value to a positive value. The positive value eddy current signal 52 continues while both coils are in the predetermined region to be tested. When the eddy current signal 52 again falls from the positive value to a zero value, an indication of the end of the region, such as the bottom of the threads, is indicated.

Figure 10:
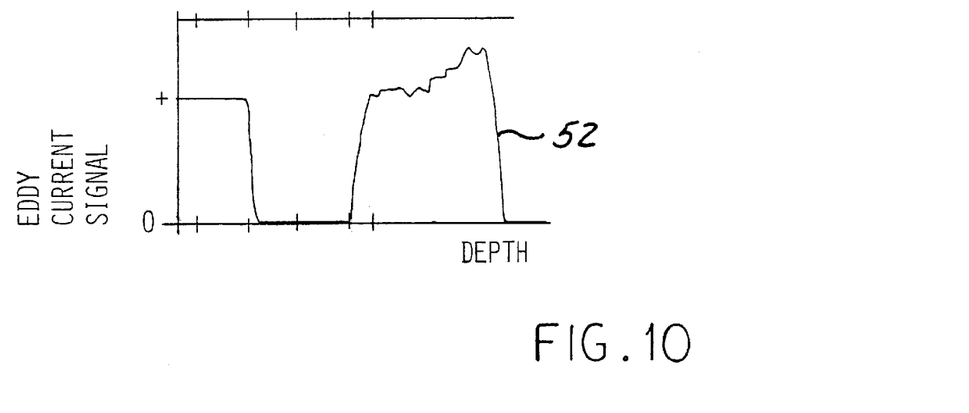
FIG. 10 is a graph illustrating an absolute value for an eddy current signal along the vertical axis versus probe depth or position along the horizontal axis for a dual coil probe according to the present invention showing a profile of an unacceptable or non-conforming threaded aperture with an anomaly near the bottom of the aperture.

Referring now to FIG. 10, an eddy current signal 54 for unacceptable or non-conforming part is illustrated. The illustrated graph is similar to that shown and described with respect to FIG. 9, and illustrates an anomalous trace along the predetermined region indicating an anomaly near the end portion of the predetermined region being tested. The unexpected rise in the eddy current signal 54 indicates an abnormality in the predetermined region being tested resulting in an indication by the comparator 40 and/or central control unit 42 of a non-conforming part.

Referring now to FIG. 11, an alternative embodiment 10a of the apparatus is illustrated. The apparatus 10a is also used for inspecting contours 12a formed along a predetermined region 14a of a surface 16a on a workpiece 18a formed of an electrically conductive material using eddy current. The probe 20a has a longitudinal axis 22a and is moveable along a path of travel with respect to the predetermined region 14a to be inspected on the workpiece 18a. At least two coils 24a, 26a, are spaced longitudinally from one another and supported by the probe 20a, to be electrically excited with a predetermined frequency and amplitude during movement of the probe 20a, along the path of travel. Means 28a is provided for measuring the excitation voltage of each coil, 24a, 26a, as eddy currents are induced in the electrically conductive material of the workpiece 18a by the coils 24a, 26a, supported on the probe 20a moving along the path of travel with respect to the workpiece 18a. Preferably, the first and second coils 24a, 26a, are disposed coaxial with respect to one another along the longitudinal axis 22a of the probe 20a. The contours 12a of the workpiece 18a can include threads 32a formed on a shaft of a workpiece 18a.

The measuring means 28a can include a first voltage sensor 36a for measuring the excitation voltage of the first coil 24a, a second voltage sensor 38a for measuring the excitation voltage of the second coil 26a, and a comparator 40a for subtracting the excitation voltage sensed by the second voltage sensor 36a from the excitation voltage sensed by the first voltage sensor 38a. The comparator 40a is provided for comparing the excitation voltage sensed by the first and second voltage sensors 36a, 38a with respect to one another. A central control unit 42a can be provided for determining if the workpiece being tested conforms to predetermined specifications in response to the measuring means 28a. The apparatus 10a according to the present invention can also include a linear variable differential transformer or linear potentiometer 44a for measuring a position of the probe 20a as the probe 20a is being moved along the path of travel with respect to the workpiece 18a. The central control unit 42a can include means for comparing the measured eddy current signals from the at least two coils 24a, 26a, where a non-zero difference after the coils 24a, 26a, have entered the predetermined region to be tested represents a bottom position of the predetermined region 14a formed on the workpiece 18a being tested.

In operation of either embodiment, a method according to the present invention is disclosed for inspecting contours 12, 12a, formed along a predetermined region 14, 14a, of a surface 16, 16a, on a workpiece 18, 18a, formed of an electrically conductive material using eddy current. The method includes the steps of moving a probe 20, 20a, having a longitudinal axis 22, 22a, along a path of travel with respect to the predetermined region to be inspected on the workpiece 18, 18a. The method also includes the step of electrically exciting at least two coils 24 or 24a, 26 or 26a, spaced longitudinally from one another and supported by the probe 20, 20a, with a predetermined frequency and amplitude during movement of the probe 20, 20a, along the path of travel. The method also includes the step of measuring the excitation voltage of each coil 24 or 24a, 26 or 26a, as eddy currents are induced in the electrically conductive material of the workpiece 18, 18a by the coils 24 or 24a, 26 or 26a supported on the probe 20, 20a moving along the path of travel with respect to the workpiece 18, 18a.

The measuring step can include the steps of measuring the excitation voltage of the first coil 24, 24a, with a first voltage sensor 36 or 36a, measuring the excitation voltage of the second coil 26 or 26a with a second voltage sensor 30 or 38a, and subtracting the excitation voltage sensed by the second voltage sensor 30 or 38a from the excitation voltage sensed by the first voltage sensor 36 or 36a with a comparator 40 or 40a. The method according to the present invention can also include the step of determining if the workpiece being tested conforms to predetermined specifications with a central control unit 42a in response to the measuring step. The method can also include the step of measuring the position of the probe as the probe is being moved along the path of travel with respect to the workpiece with a linear variable differential transformer or linear potentiometer 44a. The method according to the present invention can also include comparing measured eddy current signals from the at least two coils, where a non-zero difference after the coils have entered the predetermined region to be tested represents an end position of the predetermined region formed on the workpiece being tested.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for inspecting contours formed along a predetermined region of a surface on a workpiece formed of electrically conductive material using eddy current comprising:

a probe having a longitudinal axis, the probe movable along a path of travel with respect to the predetermined region to be inspected on the workpiece, the path of travel being defined to include a testing portion of the path extending in a direction substantially coaxial with the longitudinal axis of the probe;

at least two coils spaced longitudinally from one another and supported by the probe to be electrically excited with a predetermined frequency and amplitude during movement of the probe along the path of travel; and means for measuring the excitation voltage of each coil as eddy currents are induced in the electrically conductive material of the workpiece by the coils supported on the probe moving along the path of travel with respect to the workpiece.

2. The apparatus of claim 1 wherein the at least two coils further comprises:

first and second coils disposed coaxial with respect to one another.

3. The apparatus of claim 2 wherein the measuring means further comprises:
   a first voltage sensor for measuring the excitation voltage of the first coil;
   a second voltage sensor for measuring the excitation voltage of the second coil; and
   a comparator for subtracting the excitation voltage sensed by the second voltage sensor from the excitation voltage sensed by the first voltage sensor.

4. The apparatus of claim 1 wherein the probe is moveable within an aperture of the workpiece.

5. The apparatus of claim 1 wherein the probe is moveable to sheath a shaft of the workpiece.

6. The apparatus of claim 1 wherein the measuring means further comprises:
   a first voltage sensor for measuring the excitation voltage of one of the at least two coils;
   a second voltage sensor for measuring the excitation voltage of the other of the at least two coils; and
   a comparator for comparing the excitation voltage sensed by the second voltage sensor to the excitation voltage sensed by the first voltage sensor.

7. The apparatus of claim 1 further comprising:
   a central control unit, responsive to the measuring means, for determining if the workpiece being tested conforms to predetermined specifications.

8. The apparatus of claim 1 further comprising:
   a linear variable differential transformer for measuring a position of the probe as the probe is being moved along the path of travel with respect to the workpiece.

9. The apparatus of claim 1 further comprising:
   a linear potentiometer for measuring a position of the probe as the probe is being moved along the path of travel with respect to the workpiece.

10. The apparatus of claim 1 further comprising:
    means for comparing measured eddy current signals from the at least two coils, where non-zero differences after the coils encounter the predetermined region to be tested represent an end position of the predetermined region formed on the workpiece being tested.

11. A method for inspecting contours formed along a predetermined region of a surface on a workpiece formed of electrically conductive material using eddy current comprising the steps of:
    moving a probe having a longitudinal axis along a path of travel with respect to the predetermined region to be inspected on the workpiece, the path of travel being defined to include a testing portion of the path extending in a direction substantially coaxial with the longitudinal axis of the probe;
    electrically exciting at least two coils spaced longitudinally from one another and supported by the probe with a predetermined frequency and amplitude during movement of the probe along the path of travel; and
    measuring the excitation voltage of each coil as eddy currents are induced in the electrically conductive material of the workpiece by the coils supported on the probe moving along the path of travel with respect to the workpiece.

12. The method of claim 11 wherein the at least two coils includes first and second coils disposed coaxial with respect to one another.

13. The method of claim 12 wherein the measuring step further comprises the steps of:
    measuring the excitation voltage of the first coil with a first voltage sensor;
    measuring the excitation voltage of the second coil with a second voltage sensor; and
    subtracting the excitation voltage sensed by the second voltage sensor from the excitation voltage sensed by the first voltage sensor with a comparator.

14. The method of claim 11 wherein the moving step moves probe within an aperture of the workpiece.

15. The method of claim 11 wherein the moving step moves probe to sheath a shaft of the workpiece.

16. The method of claim 11 wherein the measuring step further comprises the steps of:
    measuring the excitation voltage of one of the at least two coils with a first voltage sensor;
    measuring the excitation voltage of the other of the at least two coils with a second voltage sensor; and
    comparing the excitation voltage sensed by the second voltage sensor to the excitation voltage sensed by the first voltage sensor with a comparator.

17. The method of claim 11 further comprising the steps of:
    determining if the workpiece being tested conforms to predetermined specifications with a central control unit, responsive to the measuring step.

18. The method of claim 11 further comprising the step of:
    measuring a position of the probe as the probe is being moved along the path of travel with respect to the workpiece with a linear variable differential transformer.

19. The method of claim 11 further comprising the step of:
    measuring a position of the probe as the probe is being moved along the path of travel with respect to the workpiece with a linear potentiometer.

20. The method of claim 11 further comprising the step of:
    comparing measured eddy current signals from the at least two coils, where non-zero differences after the coils encounter the predetermined region to be tested represent an end position of the predetermined region formed on the workpiece being tested.

21. An apparatus for inspecting contours formed along a predetermined region of a surface on a workpiece formed of electrically conductive material using eddy current comprising:
    a probe having a longitudinal axis, the probe movable along a path of travel with respect to the predetermined region to be inspected on the work piece, the predetermined region including at least one thread;
    at least two coils spaced longitudinally from one another and supported by the probe to be electrically excited with a predetermined frequency an amplitude during movement of the probe along the path of travel; and
    means for measuring the excitation voltage of each coil as eddy currents are induced in the electrically conducted material of the work piece by the coil supported on the probe moving along the path of travel with respect to the work piece.

22. The apparatus of claim 21 wherein at least two coils further comprise:
    first and second coils disposed coaxial and longitudinally spaced with respect to one another.

23. The apparatus of claim 22 wherein the measuring means further comprises:
    a first voltage sensor for measuring the excitation voltage of the first coil;

a second voltage sensor for measuring the excitation voltage of the second coil; and a comparitor for subtracting the excitation voltage sensed by the second voltage sensor from the excitation voltage sensed by the first voltage sensor.

24. The apparatus of claim 21 further comprising:

means for comparing measured eddy current signals from the at least two coils, where non-zero differences after the coils encounter the predetermined region to be tested represent an end position of the predetermined region formed on the work piece being tested.

25. An apparatus for inspecting contours formed along a predetermined region of a surface on a work piece formed of electrically conductive material using eddy current comprising:

a probe having a longitudinal axis, the probe movable along a path of travel with respect to the predetermined region to be inspected on the work piece, the predetermined region to be inspected remaining substantially stationary with respect to the movement of the probe;

at least two coils spaced longitudinally from one another and supported by the probe to be electrically excited with a predetermined frequency and amplitude during movement of the probe along the path of travel; and means for measuring the excitation voltage of each coil as eddy currents are induced in the electrically conducted material of the work piece by the coils supported on the probe moving along the path of travel with respect to the work piece.

26. The apparatus of claim 25 wherein at least two coils further comprise:

first and second coils disposed coaxial and longitudinally spaced with respect to one another.

27. The apparatus of claim 25 wherein the measuring means further comprises:

a first voltage sensor for measuring the excitation voltage of the first coil;

a second voltage sensor for measuring the excitation voltage of the second coil; and a comparitor for subtracting the excitation voltage sensed by the second voltage sensor from the excitation voltage sensed by the first voltage sensor.

28. The apparatus of claim 25 further comprising:

means for comparing measured eddy current signals from the at least two coils, where non-zero differences after the coils encounter the predetermined region to be tested represent an end position of the predetermined region formed on the work piece being tested.

* * * * *